United States Patent
Thompson et al.

(10) Patent No.: US 9,642,919 B2
(45) Date of Patent: May 9, 2017

(54) LAYERED DOUBLE HYDROXIDES

(71) Applicant: OXFORD PHARMASCIENCE LIMITED, London (GB)

(72) Inventors: Claire Thompson, Hertfordshire (GB); Marcelo Leonardo Bravo Cordero, Oxfordshire (GB); Dermot Michael O'Hare, Oxford (GB)

(73) Assignee: OXFORD PHARMASCIENCE LIMITED (GB)

( * ) Notice: Subject to any disclaimer, the term of this patent is extended or adjusted under 35 U.S.C. 154(b) by 0 days.

(21) Appl. No.: 14/433,599

(22) PCT Filed: Oct. 1, 2013

(86) PCT No.: PCT/GB2013/052554
§ 371 (c)(1),
(2) Date: Apr. 3, 2015

(87) PCT Pub. No.: WO2014/053822
PCT Pub. Date: Apr. 10, 2014

(65) Prior Publication Data
US 2015/0258212 A1    Sep. 17, 2015

(30) Foreign Application Priority Data
Oct. 5, 2012  (GB) ................................ 1217911.5

(51) Int. Cl.
C07C 53/134   (2006.01)
A61K 47/48    (2006.01)
A61K 9/14     (2006.01)
A61K 9/16     (2006.01)
A61K 31/192   (2006.01)

(52) U.S. Cl.
CPC ........ A61K 47/48961 (2013.01); A61K 9/143 (2013.01); A61K 9/1611 (2013.01); A61K 31/192 (2013.01)

(58) Field of Classification Search
CPC ............ A61K 31/192; A61K 47/48961; A61K 9/143; A61K 9/1611; C07C 51/08; C07C 57/58; C07C 51/00; C07C 45/46
See application file for complete search history.

(56) References Cited

U.S. PATENT DOCUMENTS

| 2004/0052849 | A1* | 3/2004 | O'hare ................. A61K 9/143 424/484 |
| 2006/0140994 | A1 | 6/2006 | Bagwell et al. |
| 2009/0317459 | A1* | 12/2009 | Pennel ................ A61K 9/1611 424/451 |
| 2010/0130750 | A1* | 5/2010 | Yan ..................... C07D 209/82 548/440 |
| 2010/0233286 | A1* | 9/2010 | Lu ........................ B82Y 30/00 424/600 |
| 2011/0040006 | A1 | 2/2011 | Peter et al. |

FOREIGN PATENT DOCUMENTS

| CN | 1712010 A | 12/2005 |
| CN | 1751007 A | 3/2006 |
| CN | 1947700 A | 4/2007 |
| CN | 100462071 C | 2/2009 |
| CN | 101597474 A | 12/2009 |
| CN | 101507819 B | 1/2011 |
| CN | 101493404 B | 8/2011 |
| CN | 191785860 B | 11/2012 |
| CN | 102218043 B | 3/2013 |
| EP | 0134936 * | 3/1985 |
| EP | 0134936 A | 3/1985 |
| EP | 0 550 415 B1 | 7/1997 |
| EP | 1 341 556 B1 | 10/2008 |
| WO | 02/49779 A1 | 6/2002 |
| WO | 2004/099104 A1 | 11/2004 |
| WO | 2010/089691 A1 | 8/2010 |

OTHER PUBLICATIONS

Arco et al. (Synthesis and characterization of layered double hydroxides (LDH) intercalated with non-steroidal anti-inflammatory drugs (NSAID) Journal of Solid State Chemistry 177 (2004) 3954-3962).*
Liu et al. (Liquid-Crystalline Phases of Colloidal Dispersions of Layered Double Hydroxides, Chem. Mater. 2003, 15, 3240-3241).*
International Search Report dated Dec. 17, 2013 form International Application No. PCT/GB2013/052554, pp. 1-11.
Parello, Mara L. et al. Dissolution kinetics and mechanism of Mg-Al layered double hydroxides: A simple approach to describe drug release in acid media. Journal of Colloid and Interface Science, 351 (2010), pp. 134-139.
Nalawade, Bharai et al. Layered doule hydorxides: A review. Journal of Scientific & Industrial Research. Apr. 2009, vol. 68, pp. 267-272.
Silion, Mihaela et al. In vitro and in vivo behavior of ketoprofen intercalated into layered double hydroxides. J. Mater. Sci.: Mater. Med. Med. (2010) 21:3009-3018.
Search Report dated Aug. 14, 2013 from GB Application No. 1217911.5, pp. 1-3.

(Continued)

*Primary Examiner* — Yevegeny Valenrod
*Assistant Examiner* — Blaine G Doletski
(74) *Attorney, Agent, or Firm* — MH2 Technology Law Group LLP

(57) ABSTRACT

The invention relates to layered double hydroxide (LDH) materials and in particular to new methods of preparing improved LDH materials which have intercalated active anionic compounds (improved LDH-active anion materials). The improved LDH-active anion materials are characterized by their high degree of robustness, demonstrated by their high Particle Robustness Factor values, and by their ability to retain substantially all of the intercalated active anionic compound, in the absence of ion exchange conditions and/or at pH>4.

11 Claims, 2 Drawing Sheets

(56) References Cited

OTHER PUBLICATIONS

Search Repor dated Feb. 5, 2013 from GB Application No. 1217911.5, pp. 1-5.
European Search Report dated Jul. 17, 2015 issued in European Application No. 15166388.7, pp. 1-8.
Communication dated Sep. 7, 2015 issued in European Patent Application No. 13 771 206.3, pp. 1-6.
Eurasian Office Action dated May 11,2016, Eurasian Application No. 201590673/28, filed Oct. 1, 2013, pages.
Russian Office Action for RU Appl. No. 201590673 dated Dec. 5, 2016.

\* cited by examiner

LAYERED DOUBLE HYDROXIDES

CROSS-REFERENCE TO RELATED APPLICATIONS

This application is a National Phase application of PCT application no. PCT/GB2013/052554 filed Oct. 1, 2013, which application claims priority to Great Britain Application No. 1217911.5 filed Oct. 5, 2012, the entire contents of which are herein incorporated by reference. The PCT application published as International Publication No. WO 2014/053822 on Apr. 10, 2014.

FIELD OF THE INVENTION

The present invention relates to layered double hydroxide (LDH) materials and in particular to a new method of preparing LDH materials in which active anionic compounds are intercalated (LDH-active anionic compounds). Further the present invention relates to novel LDH-active anionic compounds which are characterised by their high degree of robustness, and by their ability to retain the intercalated active anionic compound. The invention also relates to the use of such novel LDH-active anionic compounds in, for example, active anionic compound-storage and/or active anionic compound-carrier and/or active anionic compound-delivery systems; to formulations comprising LDH-active anionic compounds and especially to formulations comprising LDH-active anionic compounds which require the taste, irritation or other unwanted/adverse properties of the active anion to be masked and/or reduced.

BACKGROUND OF THE INVENTION

A review of layered double hydroxides (LDHs) is given in Chemistry in Britain, September 1997, pages 59 to 62. Briefly, these materials are either mixed hydroxides of monovalent and trivalent metals or mixed hydroxides of divalent and trivalent metals, having an excess of positive charge that is balanced by interlayer anions. Such materials can be represented either by:

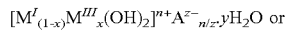

$[M^I_{(1-x)}M^{III}_x(OH)_2]^{n+}A^{z-}_{n/z}.yH_2O$ or

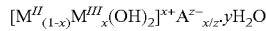

$[M^{II}_{(1-x)}M^{III}_x(OH)_2]^{x+}A^{z-}_{x/z}.yH_2O$ where $M^I$, $M^{II}$ and $M^{III}$ are mono-, di- and trivalent cations respectively, that occupy octahedral positions in hydroxide layers; $A^{z-}$ is an interlayer charge-compensating anion; z is an integer; n=2x−1; x is less than 1; and y is ≥0.

The methods of manufacturing LDH materials are well documented and include ion exchange, co-precipitation, rehydration, secondary intercalation, re-coprecipitation, and templated synthesis—see for example He et al., Struct. Bond, 2006, 119, p. 89-119. More recently, US2010/0233286 A1 (Lu and Xu) describes that co-precipitation is known to involve the steps of forming a mixed metal ion solution containing the appropriate metal ions and adding this into an alkaline material, e.g. an alkaline solution, to form LDH particles. Generally, the alkaline solution is a sodium hydroxide solution, optionally with either sodium bicarbonate or sodium carbonate, however others are also known, for example ammonia solutions, KOH, NaHCO$_3$, KHCO$_3$, Na$_2$CO$_3$, K$_2$CO$_3$ and organic amines such as methylamine and ethylamine. Using this method, it is possible to produce LDH materials intercalated with one or more simple anions such as, Cl$^-$ (derived from the counter chloride salt of the metal chloride starting material) NO$_3^-$ (derived from the counter nitrate salt of the metal nitrate starting material) and CO$_3^-$ (derived from NaCO$_3$ used as part of the alkaline solution). More often, the LDH product contains a mixture of intercalated anions, for example when a solution of MgCl$_2$ and AlCl$_3$ is co-precipitated with an alkaline solution containing NaOH and Na$_2$CO$_3$, then Mg$_3$Al(OH)$_8$(CO$_3$)$_{0.5}$.H$_2$O is produced, i.e. an LDH material intercalated with CO$_3^-$ ions. Another feature of U2010/0233286 A1 is the treatment of the LDH particles with a "hydrothermal" step. This is described as a way to reduce the size of the LDH particles and to ensure that they conform to a narrow particle size distribution of ±20% around the average size. The resulting product forms a stable and well dispersed suspension of LDH particles in water. The hydrothermal treatment involves dispersing the LDH material formed by a co-precipitation process in water and heating this dispersion to a temperature of from greater than 80° to 150° C. in an autoclave for a period of 1 hour to 144 hours. During this prior art process, boiling is preferably suppressed. The modified LDH particles may be recovered from the hydrothermally treated suspension by removing the water, for example by drying, filtration or centrifugation, and then drying the separated LDH particles.

Co-precipitation followed by an additional ion exchange process is reported to be one way to introduce larger, more complex interlayer anionics into the LDH materials. For example, EP0987328(B1) (Choy and Kwak) describes an LDH/bio-inorganic hybrid composite that is capable of storing and carrying genes such as nucleoside-5'-monophosphate, nucleoside-5'triphosphate, DNA and RNA and is prepared using three steps: a first step involving co-precipitation in which an alkaline material is added to an aqueous mixed metal solution comprising a bivalent metal ($M^{II}$) (e.g. Mg(NO$_3$)$_2$) and a trivalent metal ($M^{III}$) (e.g. Al(NO$_3$)$_3$). A second step which isolates the reaction product from the first step; that is, a stable layered double hydroxide (LDH) intercalated with charge compensating anions (derived from the original bi- and trivalent metal starting materials (e.g. OH$^-$, NO$_3^-$)). And a third step in which these intercalated compensating anions are subjected to an ion exchange reaction with the anionic species of the desired gene, DNA or RNA. Compounds of the general formula $[M^{II}_{(1-x)} M^{III}_x(OH)_2)][A_{BIO}{}^{0-}]_{x/n}.yH_2O$ are produced. A very similar co-precipitation/ion exchange process is described for example in WO2010/089691A1 which apparently produces "highly crystalline" stearate and oleate intercalated layered double hydroxides, in CN101597474B which describes glyphosine-LDHs with "good crystal phase structure" and in EP0550415 A2 which describes a uniform layered double hydroxide intercalated by polyoxometalate. However as described below, the present applicant has found that in practice, even though LDH-active anion materials made by this method do appear to be crystalline, the degree of robustness exhibited by these products is significantly less than is observed in the improved LDH-active anion materials of the present invention, and in any case does not provide materials that are capable of solving the problems addressed by the present invention.

Other prior art, for example EP 1341556(B1) teaches the preparation of a drug delivery system comprising LDH materials intercalated with pharmaceutically-active anionic compounds which again uses a similar co-precipitation/ion exchange method described above and starts with a host LDH compound such as [LiAl$_2$(OH)$_6$]Cl.H$_2$O or Ca$_2$Al(OH)$_6$NO$_3$.xH$_2$O, (presumably made via a co-precipitation reaction), and then uses an ion exchange reaction in which the host LDH is reacted with a sodium salt of the desired pharmaceutically active anionic compound. The intercalated LDH-pharmaceutically-active anion material is separated from the reaction mixture by filtration, then washed with an excess of deionised water and acetone and allowed to dry in air. The advantage of such LDH-active anion materials is described to be their ability to release their active anionic compounds slowly to produce sustained/controlled release drug delivery systems. As the results in this prior art show, at pH 4 and 7 such LDH-pharmaceutically-active anion materials release 60-80% of the pharmaceutical within the first 5 minutes, and then release the remaining 20-40% over the period of 40 to 60 minutes.

The study reported by Silion et al in Journal of Materials Science, Vol. 21 (11), 2010 concerns the in vitro and in vivo behavior of ketoprofen intercalated into LDH materials. The intercalated materials are made using the same ion exchange method described above, and as the broad XRD peaks and release profiles in this publication demonstrate, the materials tested are of a poor ordered structure. Moreover, the intercalated materials release about 10% of the ketoprofen in around 30 minutes at pH7.4, and the remaining ketoprofen is released over time.

Chinese patent CN1299616C describes making LDH materials intercalated with food preservative compounds via a co-precipitation process, involving the steps: reacting di- and tri-metal salts and a food preservative substance (FP) with sodium hydroxide at pH 7-12, under nitrogen and heating between 15 and 150° C. for 2 to 72 hours to yield the desired FP-LDH material. The purpose of these FP-LDH materials is to provide for the slow release (1 to 60 days) of the food preservative into food. The Figures show that at a pH of 4.5 and above, 10% or more of the food preservative substance is released almost immediately, and the remainder leaches over a period of several hours. The XRD patterns record low intensity (CPS) values which is an indication that the FP-LDH materials made by this prior art are not robust.

Chinese patent CN 1297276C discloses the preparation of slow releasing intercalated 5-aminosalicilic acid (5-ASA)-LDH materials via a co-precipitation process: two soluble metallic salts and 5-aminosalicilic acid are reacted with sodium hydroxide at pH 6-10 and heated at 15 to 70° C. for 12 to 72 hours. The slow release results presented in FIG. 3 demonstrate that at pH 6.9, as much as 40% of the 5-ASA is released almost immediately and the rest is released over time. The broad peaks of the XRD in FIG. 1 indicate that the 5-ASA-LDH material produced according to this prior art has an extremely low robustness.

Chinese patent CN 101785860B teaches two preparative methods for making Tegafur/LDH nanometer hybrid materials that exhibit slow release of the medicament Tegafur. A first method involves the co-precipitation of di- and tri-metallic salts with Tegafur under alkaline conditions and then recovering the desired Tegafur/LDH material. The second method makes an LDH material from two metallic salts in a first step, and this is followed by a second step in which Tegafur is intercalated into the LDH material by an ion-exchange reaction. The slow release characteristics of the materials presented in FIG. 4 show that almost 60% Tegafur is released after about 30 minutes at pH 7.2 and this is up to about 90% at pH 4.8 after about 30 minutes. The low intensity values and broad peaks in the XRDs reveal that the Tegafur-LDH materials made as described in this prior art are of poor robustness.

Chinese Patent document CN 100462071C describes preparing magnetic Brufen-LDH materials which again provide the sustained release of ibuprofen. The method involves co-precipitating metal salts in an alkaline environment (e.g. NaOH) to give the LDH and then introducing into this the ibuprofen and an iron containing material, and recovering product materials with a high specific magnetisation by filtration followed by washing and drying.

Chinese patent CN 102218043B describes sustained release tablets comprising dextran-LDH-aspirin materials that are made by heating di- and tri-metal salts with aspirin at 70 to 80° C. in sodium hydroxide (pH 10 to 12) under nitrogen for 40 minutes. The resulting slurry is then heated with a dextran solution at a temperature of 70 to 85° C. under nitrogen and with stirring. The process to isolate and purify the desired final product is described as pouring the dextran-LDH-ASP mixture into cold ethanol at a temperature of from −20 to −10° C., allowing this to stand for 1 hour in a freezer and then at room temperature for 30 minutes before adding doubly distilled water and centrifuging to separate the solid phase. The latter is then separated, washed with ethanol and dried at 65 to 80° C. 0.085 Mpa in a vacuum oven. As FIGS. 1, 2 and 3 in this patent illustrate, at least 10% of the aspirin is released after about 30 minutes no matter whether the pH is 1.0, 6.8 or 7.0; and 80% or more of the aspirin is released after about 16 hours.

CN101507819B describes what it calls a hydrothermal synthesis method for making hydrotalcite (LDH) materials intercalated with ibuprofen. Metal salts are co-precipitated with ibuprofen under alkaline conditions, pH 9 to 11 and with heating to 100 to 180° C. for 18 to 72 hours. The resulting product is then isolated and dried at 60-80° C. for 24 to 72 hours. This method favours the production of particles sized 300-600 nm and the document reports that increasing the particle size, decreases the rate that ibuprofen is released.

WO2004/099104 describes the use of clay materials such as LDH materials to sequester waste material containing manure from animal feedlots. The resulting material can then be dried and granulated, and as this document states: because the anion and cations are unlikely to be permanently affixed to the LDH, they are slowly released into the environment.

To summarise: it is evident from the wealth of literature and patent publications discussed above, that it is well known to use intercalated LDH-active anion materials as a means to slow down the release of an active anionic compound and thereby to provide controlled release preparations. However, the present invention is not concerned with providing such preparations. Instead the present invention is concerned with developing improved LDH-active anion materials that are extremely robust, as defined below, and that are non-leaching. By "non-leaching" we mean that the improved LDH-active anion materials of the present invention are on the one hand capable of delivering the active anion at pH 4 or below, but are on the other hand capable of retaining substantially all of the active anionic compound within the LDH structure when present in an environment where ion exchange conditions are absent and/or at above pH 4. The present invention is particularly concerned with improved LDH-active anion materials that, in the absence of ion-exchange conditions and/or at a pH>4, do not release any significant amount of the active anionic compound over time; it is substantially retained within the LDH matrix. The preparations covered by the present invention can include, but are not limited to, active anions with pharmaceutical and/or non-pharmaceutical activity, and includes any active anion which is required for reasons of health, safety, toxicity, ease of use and/or ease of handling to be substantially retained within the LDH matrix when ion exchange conditions are absent and/or the pH is >4. Poor taste, bitterness, burn and irritation within the mouth, buccal cavity, larynx or gastrointestinal tract are issues for a number of orally delivered formulations of drug classes including, but not limited to, non-steroidal anti-inflammatory drugs NSAIDs) gaba-analogues and antibiotics. These issues lead to non-compliance in patients, in particular within pediatrics patient groups. Furthermore, as well as pharmaceuticals, there are numerous food and beverage products and bulking agents that have unpleasant and bitter tasting components which hinder the acceptability of these ingredients to the consumer.

Hereafter "poor tasting or irritating substance" is used to define any ingredient which may or may not be pharmaceutically active, which results in any unacceptable taste, bitterness, burn, irritation or any other unacceptable sensation being experienced by the consumer or patient within the mouth, buccal cavity, larynx or gastrointestinal tract, either on its own or in any medicament, health supplement, pharmaceutical, non-pharmaceutical, food, or beverage formulation, preparation or recipe.

Prior art methods to improve the palatability of poor tasting or irritating substances in orally delivered pharmaceutical and/or other edible formulations use a number of different taste masking strategies to effectively over ride, conceal or reduce the availability of the poor tasting or irritating substance to the taste buds and/or other receptors in the mouth, buccal cavity, larynx or gastrointestinal tract of the consumer. For example, in tablet and non-tablet products (e.g. syrups, suspensions, liquids and orally disintegrating granules) taste masking may involve the addition of extra ingredients such as flavours, sweeteners and amino acids to the formulation. Alternately, either the particles of the poor tasting or irritating substance or the entire formulation, for example the powder or the tablet, may be encapsulated with a coating selected from a wide variety of polymers, for example polymeric hydrophilic or lipophilic materials such as starch, gelatine, lecithin, methylcellulose or ethylcellulose. Other taste masking techniques use conventional granulation; spray congealing with lipids; the formation of complexes with cyclodextrins, liposomes, ion-exchange resins; freeze drying processes; multiple emulsions; salts and polymeric membranes. A review of taste masking methods is given in Sohi et al., Drug Development and Industrial Pharmacy, 2004, 30, 5 pp 429-448.

When taste masking poor tasting or irritating substances in oral formulations using coating methods, the goal is to cover the poor tasting or irritating substance, or the entire formulation, with a coating that will remain in place for as long as the formulation is in the mouth of the patient or consumer, but not so long that it interferes with the dissolution profile of the active anionic compound as this could, where the active anionic compound is an active pharmaceutical, compromise drug efficacy. As well as this potential pitfall, coating also adds significant cost both as a result of using added ingredients but also as a result of the extra processing time needed for manufacture. Coated materials in the form of microcapsules can also be unstable and may rupture in liquid systems.

Taste, burn and/or irritation masking via complexation involves the poor tasting or irritating substance forming a complex at a molecular level with a complexing agent. Essentially, the complexing agents weakly bind the poor tasting or irritating substance using Van der Waals forces and thereby reduce the degree to which the poor tasting or irritating substance is exposed to the taste buds, mouth, buccal cavity, larynx or gastrointestinal tract. Prior art disclosing this technique includes: JP03,236316 (Kurasumi et al.); U.S. Pat. No. 5,024,997 (Motola et al.); JP02291244 (Ikezuki); Manek and Kamat, *Indian J. Pharm. Sci.*, 1981, 43, 11-12, 209-212; EP0501763 (Honeysett et al.); U.S. Pat. No. 6,514,492 (Gao et al.); Agarwal et al., *Drug Dev. Ind. Pharm.*, 2000, 26, 7, 773-776.

However, complexation technologies again add to the cost and time of manufacturing and they are only suitable for formulations that contain relatively small amounts of the poor tasting or irritating substance, such as in low dosage drugs. In addition, complexation does not usually encapsulate the entire structure of the poor tasting or irritating substance and leaves parts of the structure free to interact with cell receptors in the mouth, buccal cavity, larynx or gastrointestinal tract. Hence, taste, bitterness, burn, or irritation may not be completely negated by this method.

As with coatings, complexing agents can affect the release profile of the poor tasting or irritating substance and this, as mentioned above, can have an effect on drug efficacy where the poor tasting or irritating substance is a pharmaceutically active material. For example, ion exchange resin complexes can be designed to release the complexed pharmaceutically active material by exchanging with appropriately charged ions within the gastrointestinal tract (GIT), in this way they allow diffusion of the free pharmaceutically active material from the resin. This exchange may not provide immediate release of the drug from the formulation and this will hamper the drug dissolution profile.

The prior art also describes several methods to determine the extent to which a substance is poor tasting, for example an assay for bitter taste function is reported by J. D. Boughter Jr et al, in Chemical Senses 2001, Vol 27, issue 2 pp 133-142; and the company Opertech Bio, Inc provides details of a high throughput system for measuring taste quality and palatability on its website, opertechbio.com.

The present invention is directed to new improved intercalated LDH-active anion materials, in particular those which are extremely robust and highly resistant to the leaching of the active anionic compound from the LDH, in the absence of ion-exchange conditions and/or in an environment above pH 4. Such improved materials are useful in a wide range of storage, carrier and delivery system applications, including pharmaceutical and non-pharmaceutical applications.

The present invention is also directed to a simple, cost effective and reliable process for the manufacture of improved intercalated LDH-active anion materials which are extremely robust and highly resistant to leaching, especially in the absence of ion exchange conditions and/or under conditions of above pH4.

The present invention is particularly directed to providing highly effective taste, burn and/or irritation masked compositions, for both pharmaceutical and non-pharmaceutical applications.

The terms "active anionic compound" and "active anion" are used interchangeably herein and shall be interpreted to include any molecule or compound that is anionic (i.e. a molecule with a negative charge) or that has an anion generating moiety, for example a salt of an anionic molecule. An anionic compound or anion is interpreted herein to be "active" in the sense that it produces a chemical, physical, physiological or pharmaceutical effect. This effect may or may not be recognised in an animal or human body. Suitable active anionic compounds may be simple anions whereas others may be larger and/or have structures which are more complex than simple anions and may include, but are not limited to, dye compounds, agrochemicals, additives used in medicaments, food supplements and vitamin supplements, food or beverages and pharmaceuticals, all for human or animal use. Preferred active anionic compounds that produce a pharmaceutical effect and may include, but are not limited to, the classes of NSAIDS, gaba-analogues, antibiotics, statins, angiotensin-converting enzyme (ACE) inhibitors, antihistamines, dopamine precursors, anti-microbials, psychostimulants, prostaglandins, anti-depressants, anti-convulsants, coagulants, anti-cancer agents, immunosuppressants and laxatives.

The Applicant has found that the robustness and performance characteristics of LDH-active anion materials, such as those made by any known method for example a co-precipitation process to make the LDH followed by an ion exchange reaction to intercalate the active anion, or a single step co-precipitation process involving the active anion and the metal salts, are be transformed and significantly improved using a specific mixing, heating, washing and drying procedure which is the present invention, into highly robust and essentially non-leaching LDH-active anion materials, specifically in the absence of ion exchange conditions or at a pH above 4.

Thus the present invention provides a process for the manufacture of improved LDH-active anion material, comprising the steps of:
a) dispersing an LDH-active anion starting material in a liquid dispersant, then heating and agitating the resulting suspension;
b) cooling the heated suspension and separating the heat treated LDH-active anionic material from the suspension;
c) washing the heat-treated LDH-active anionic compound and drying to constant weight to yield improved LDH-active anion material.

Suitable liquid dispersants include deionised water, and any other liquid which does not dissolve either the starting or improved LHD-active anion material. Any suitable reaction vessel may be employed. The preferred reaction vessel is an autoclave, a pressure vessel, or a standard reaction vessel, and this may be under an inert atmosphere, e.g. nitrogen, at any suitable pressure. Specifically, high pressure conditions are not essential. The ideal temperature used in step a) is either a specific temperature, or a range of temperatures, and is between 50° C. and 200° C., preferably between 80° C. and 180° C. and most advantageously at 150° C.

Agitation in step a) is a critical step in the process. The hydrothermal process described in the prior art does not implicitly or explicitly hint, disclose or suggest the need for agitation, and the Applicant has demonstrated in the specific Examples below that when agitation is absent then the robustness of the resulting product is too low to provide the non-leaching benefits of the present invention. "Agitation" includes any means any suitable means which serves to mix, turn or generally move the reactants in step a) about during the process to produce the improved LDH-active anion material. Preferred means of agitation include one or more of vibration, shaking and vigorous stirring. A desirable stirring rate is in the range 800 rpm to 1200 rpm. "Agitation" is important to facilitate good transfer of heat within the suspension to generate annealed, robust particles. Thus "agitation" also includes any means which facilitates good transfer of heat within the suspension formed in step a) to generate robust particles.

The period of heating can be between 1 and 72 hours, preferably less than 8 hours and ideally around 2 hours.

After cooling to room temperature, the heat treated LDH-active anion material may conveniently be separated from the suspension using vacuum filtration, and the resulting improved LDH-active anion material is obtained after washing the separated heat-treated material one or more times with a liquid to remove any residual free active anionic compound from the surface; suitable liquids to achieve this include deionised water. Further improved results are obtained when a further washing liquid is used, for example methanol or acetone to remove residual water from the surface of the improved LDH-active anion material.

Preferably drying in step c) is performed on material that has been sieved, de-lumped and/or crushed to break down any lumps; this ensures an efficient the drying process which again gives further improved results. Drying may be carried out under vacuum and ideally at an elevated temperature of at least 50° C., and yet further enhancements are obtained when the product is agitated during the drying procedure.

Although as described above, the LDH-active anion starting material may be made using any known method, the applicant has found particular advantage in using a single step co-precipitation reaction involving the steps:
i) forming a first mixed metal ion solution containing a) one or more trivalent metal cations, and b) one or more divalent metal cations;
ii) forming a second solution containing one or more active anionic compounds;
iii) heating the resulting second solution to a temperature above 25° C.;
iv) combining the first mixed metal ion solution with the warmed second solution with vigorous stirring; and collecting the resultant precipitated LDH-active anion material.

The trivalent metal cations comprise metal ions of valence 3+; preferred examples include $Al^{3+}$, $Co^{3+}$, $Fe^{3+}$, $Mn^{3+}$, $Ga^{3+}$, $RH^{3+}$, $RU^{3+}$, $Cr^{3+}$, $V^{3+}$, $La^{3+}$, $Y^{3+}$, $Gd^{3+}$ and $La^{3+}$. The divalent metal cations comprise metals ions of valence 2+; preferred examples include $Fe^{2+}$, $Co^{2+}$, $Ni^{2+}$, $Cu^{2+}$, $Zn^{2+}$, $Mn^{2+}$, $Pd^{2+}$, $Ti^{2+}$, $Ca^{2+}$, $Cd^{2+}$ and $Mg^{2+}$.

The preferred one or more trivalent metal cations comprise $Al^{3+}$ and/or $Fe^{3+}$ and/or $Co^{3+}$, and the one or more divalent metal cations comprise $Mg^{2+}$ and/or $Ca^{2+}$ and/or $Zn^{2+}$. Preferred di-/tri-valent cation pairs are $Mg^{2+}$—$Al^{3+}$, $Ca^{2+}$—$Al^{3+}$ and $Zn^{2+}$—$Al^{3+}$.

The first mixed metal ion solution may be prepared using any known technique, for example by dissolving salts of the relevant metals in a suitable solvent; such salts may include chlorides, nitrates, sulfates, carbonates and any other convenient and soluble metal salt. The preferred metal salts are metal nitrate, sulfates and chlorides; it is not necessary to use the same type of salt for each metal ion. The preferred solvent is water although any other solvent, or mixture of solvents, which dissolves the metal salts may be used. Alternatively, appropriate metals may be dissolved in one or more acids such as, but not limited to, HCl, $HNO_3$, $H_2SO_4$, or organic carboxylic acids for example methanoic acid and acetic acid.

It is advantageous if one or both of the first mixed metal ion solution and the second solution containing the one or more active anionic compounds are prepared and maintained under an inert atmosphere. It is desirable that the solvents used in each of the first and second solutions are at least miscible with one another, and it is especially convenient if both solvents are the same; water is preferred.

The second solution may be heated to a specific temperature, or within a range of temperatures, between 25° C. and 100° C., preferably between 30° C. and 80° C., ideally between 55° C. and 65° C., and most advantageously at 60° C.

When preparing the second solutions and also throughout the combination of the first and second solutions, it is important to keep the active anionic compound dissolved in the reaction solution; this may be achieved, for example, by adjusting the pH of the reaction mixture. The exact pH needed will depend on the solubility profile of the particular active anionic compound, for example when Ibuprofen is the active anionic compound then the pH of 9.5 or above is preferred and similar conditions are beneficial for Naproxen and Diclofenac.

In a preferred process, the first mixed metal ion solution is added to the warmed second solution in Step iv) using relatively slow, for example drop-wise, addition. However the addition of the mixed metal ion solution should be completed within 4 hours and ideally within 1 to 2 hours. For best results, the resulting reaction mixture obtained at the end of the addition step iv) should be stirred, preferably under an inert atmosphere, for at least 10 minutes.

The resultant precipitate containing LDH-active anion material is conveniently recovered from the reaction mixture by vacuum filtration and is washed, preferably at least twice, with water and vacuum filtered to dry.

This method advantageously produces an LDH-active anion material in what is effectively a single co-precipitation step using readily available and inexpensive starting materials. Unlike other prior art methods discussed above, this method does not involve a first co-precipitation process to form an initial LDH material which comprises a simple intercalated anion such as $NO_3^-$, $Cl^-$, $CO_3^-$ which must be isolated and purified before employing a second ion-exchange process to intercalate the larger and/or more complex active anionic compound within it.

Moreover, the Applicant has advantageously found that the LDH-active anion materials made using a one-step co-precipitation method produce even more robust improved LDH-active anion materials as compared against improved LDH active anion materials made using other co-preciptation/ion exchange methods.

As previously mentioned, the process of the present invention produces significantly improved LDH-active anion materials with very highly robust structures and extremely low total leaching characteristics that are completely different from analogous LDH-active anionic compounds made using any of the methods in the prior art discussed above, (including the co-precipitation process followed by the hydrothermal steps disclosed in US2009/0108233 and US2010/0233286).

The difference between the improved process of the present invention and the hydrothermal steps disclosed in US2009/0108233 and US2010/0233286 is in some respects a subtle one, however as demonstrated below in the specific Examples the specific heating, agitation, drying and washing steps identified by the Applicant have a profound effect on the robustness and leaching characteristics of the product and provides LDH-active anion materials that are suitable for use in applications where the prior art materials have been shown to fail.

It is well known that all particulate substances exhibit a unique x-ray powder diffraction pattern which can be used to characterise the material and provide a finger print for identification purposes. In these diffractograms, the sharpness and intensity of the peaks is an indication of crystal structure and molecular order. Indeed partially ordered materials have very broad peaks and in amorphous materials the diffractogram has few or no distinguishable peaks.

The Scherrer equation is used in x-ray diffraction and crystallography to correlate the size of sub-micrometer particles or crystallites in a solid to the broadening of a peak in a diffraction pattern. In the Scherrer equation, $$\tau = \frac{K\lambda}{\beta \cos\theta}$$

where tau ($\tau$) is the mean size of the ordered domains, K is the shape factor, $\lambda$ is the x-ray wave length, $\beta$ is the line broadening at half the maximum intensity (FWHM) in radians and $\theta$ is the Bragg angle in radians. Larger values of tau ($\tau$) indicate a more highly ordered structure of the particulates, and this in turn indicates a more robust material. Here the applicant has used the tau values to calculate a Particle Robustness Factor. The larger the value of tau, the higher the Particle Robustness Factor.

As discussed below, the Applicant has used x-ray powder diffraction to demonstrate that differences exist between the robustness of the structure of the improved LDH-active anion materials produced following the optimised heating, washing and drying procedure of the present invention on the one hand, and the robustness of the structure of analogous LDH-active anion materials made according to the prior art, without the optimised heating, washing and drying procedure on the other. Specifically, the Applicant has used the Scherrer equation to determine the value of tau for each of the four most dominant peaks obtained by x-ray powder diffraction, and from this has calculated an average value of tau across these four most dominant peaks. As noted above, the higher the average tau value, the higher the degree of robustness demonstrated by the Particle Robustness Factor. As explained in the specific examples below, all tau values have been normalised using a zero background intensity silicon wafer standard.

Thus, the present invention provides improved LDH-active anion materials which exhibit a Particle Robustness Factor, i.e. an average value for tau for the four most dominant peaks obtained by x-ray powder diffraction, of at least 4.0 when normalised using a zero background intensity silicon wafer standard.

Preferred Particle Robustness Factor values of a least 5.5 and values of at least 7.0 are especially preferred.

During the course of their investigations the Applicant has recognised that LDH-active anion materials with a Particle Robustness Factor of at least 4.0 (determined as described above) are extremely efficient at retaining the intercalated active anionic compound within their structure, i.e. they exhibit exceedingly low levels of leaching of the active anionic compound.

Leaching is the percentage by weight of the active anionic compound that is released from the LDH-active anion material, in the absence to ion exchange conditions and/or at a pH>4, preferably at least pH 4.5, further preferably at least pH 5.0 and particularly preferably at least pH 5.5.

Materials which have low leaching characteristics are highly beneficial for end-use applications where any leached active compound would produce a deleterious effect, for example, but not limited, to taste masking applications e.g. in oral pharmaceutical and/or food and/or beverage applications, where burn, foul taste or irritation in the mouth, buccal cavity, larynx or gastrointestinal tract may be caused, and in other applications where the active anionic compounds must be retained within the LDH, for reasons such as safety, toxicity, environmental sensitivity, ease of handling etc.

Therefore, the present invention provides an improved LDH material intercalated with one or more active anionic compounds (LDH-active anion material), which leaches a total of less than 5% by weight of the amount of one or more active anionic compounds into a solvent when the improved LDH-active anion material is washed with a solvent suitable for dissolving the one or more active anionic compounds, in the absence of ion exchange conditions and/or at a pH>4.

Preferably, a total of less than 2%, highly preferably a total of less than 1% and ideally a total of less than 0.5% by weight, of the one or more active anionic compounds leaches into a solvent suitable for dissolving the one or more active anionic compounds, when the improved LDH-active anion materials is washed with the solvent, in the absence of ion exchange conditions and/or at a pH>4.

It will be noted that a "total" of at less than 5% of the active anionic compound leaches from the improved LDH-active anion materials of the present invention. This means that the improved materials of the present invention do not release any more than less than 5%; in particular there is not the continuous slow release of active anionic compound which is reported for the slow release materials in the prior art. Specifically, the active anionic compound in the improved LDH-active anion materials of the present invention is substantially retained whilst ion exchange conditions are absent and/or the pH is >4.

The Applicant has observed that total leaching levels of less than 5% by weight are typically exhibited by improved LDH-active anion materials with Particle Robustness Factor values of at least 4.0. Thus improved LDH-active anion materials with PRF of at least 4 make ideal materials where taste, burn and/or irritation needs to be masked or where the active anionic compound needs to be retained to prevent some other unwanted effect, such as toxicity, environmental sensitivity, ease of handling etc. Preferred total levels of leaching of less than 2% by weight are observed for LDH-active anionic compounds with Particle Robustness Factor values of at least 5.5 and highly preferred total levels of leaching of less than 0.5% by weight are observed for LDH-active anionic compounds with Particle Robustness Factor values of at least 7.0.

The present invention further provides an improved LDH-active anion material for use as a storage system, a carrier or a delivery system for active anionic compounds which need to be substantially retained within the LDH matrix whilst in the absence of ion exchange conditions and/or at a pH>4.

One particularly useful example is the provision of a taste, burn and/or irritation masked composition comprising an improved LDH-active anion material which exhibits an average particle robustness value, i.e. an average value for tau based on the four most dominant peaks obtained by x-ray powder diffraction, of at least 4.0 when normalised using a zero background intensity silicon wafer standard.

Such taste, burn and/or irritation masked compositions are found to improve the palatability of poor tasting or irritating substances in orally delivered pharmaceutical and/or food and/or beverage applications. The pH level of a person's mouth varies depending on what has recently been consumed and on their general oral health. A pH of 5.5 or above is generally considered to be normal, as is a pH in the range 5.6 to 7.9.

In a further aspect, the present invention provides a taste masked composition comprising an improved LDH-active anion material which leaches a total of less than 5% by weight, preferably a total of less than 2% and highly preferably a total of less than 0.5% of the one or more active anionic compounds into a solvent suitable for dissolving the one or more active anionic compounds, when the improved LDH-active anion material is washed with the solvent.

The taste, burn and/or irritation masked compositions described above may be formulated in any oral or non-oral form such as, but not limited to, dry granules, tablets, an aqueous solution or suspension, a non-aqueous solution or suspension, a syrup or a gel.

EXAMPLE 1

The Preparation of $Mg_2Al(OH)_6(C_{13}H_{17}O_2).nH_2O$ Ibuprofen Aluminium Magnesium Hydroxide by the Ion Exchange process described in EP1341556

Figure 1:
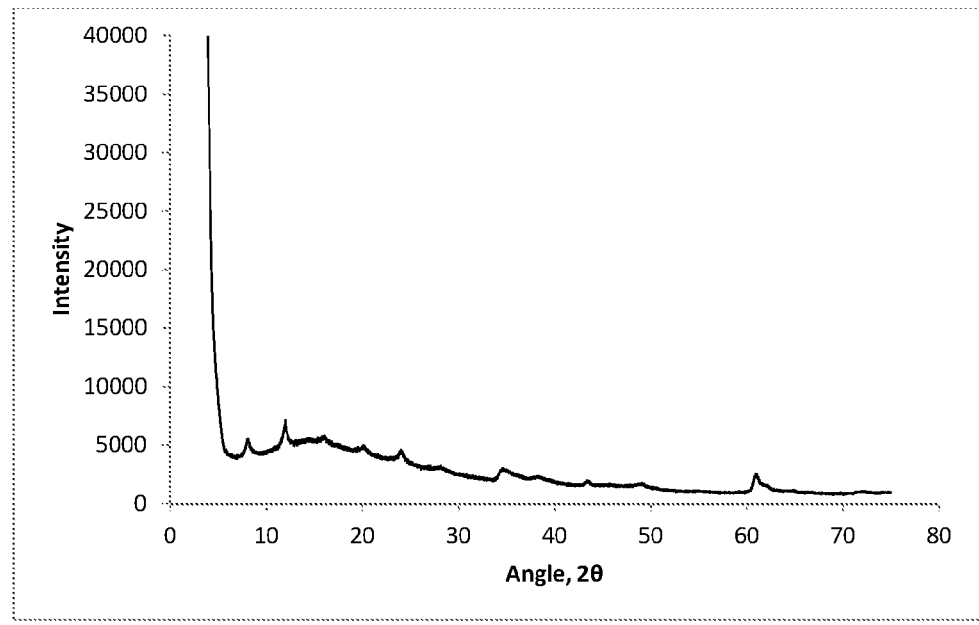
FIG. 1 shows a typical X-Ray Powder Diffractogram of an LDH-Ibuprofen material made using the ion exchange process of the prior art.

Starting Materials:
$Mg_2Al(OH)_6(NO_3)$, MgAl—$NO_3$: 0.885 g; 3.69 mmol
$C_{13}H_{18}O_2$, Ibuprofen: 1.521 g; 7.38 mmol
NaOH, Sodium Hydroxide: 0.295 g; 7.38 mmol
Method:
The MgAl—$NO_3$ was added to 25 ml of distilled $H_2O$ in a round bottomed flask which was then sealed under $N_2$ gas and sonicated for 15-30 minutes to form a suspension of MgAl—$NO_3$. A separate solution of ibuprofen was made by adding the ibuprofen with stirring to a solution of the NaOH dissolved in 25 ml of distilled $H_2O$, whilst bubbling through with $N_2$ gas on complete addition the $N_2$ gas was bubbled through for a further 5-10 minutes. The alkaline sodium Ibuprofen solution was then added to the MgAl—$NO_3$ suspension and the stirred mixture was heated to 60° C. under a flow of $N_2$ gas. Once at 60° C., the reaction vessel was sealed under $N_2$ and stirred for a further 48 hours. Effort was made to maintain stirring of the mixture throughout. The resulting reaction mixture was then vacuum-filtered and the recovered Ibuprofen Aluminium Magnesium Hydroxide product washed with distilled $H_2O$, and then acetone and finally allowed to air-dry. A typical XRP Diffractogram for this material is shown in FIG. 1.

EXAMPLE 2

Figure 2:
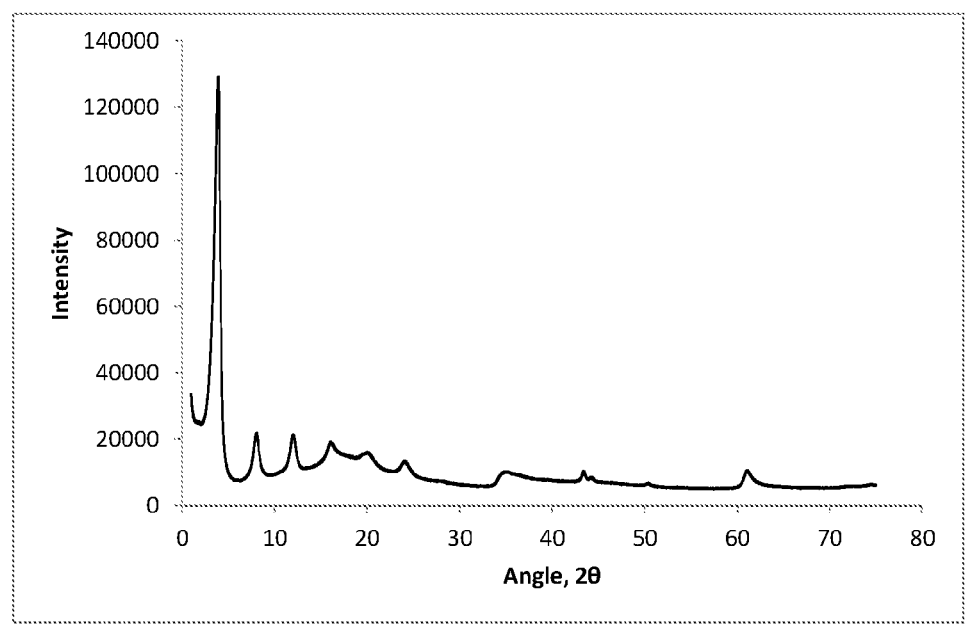
FIG. 2 shows a typical X-Ray Powder Diffractogram of LDH-Ibuprofen material produced by a Co-precipitation process.

The Preparation of $Mg_2Al(OH)_6(C_{13}H_{17}O_2).nH_2O$ (MgAl-Ibuprofen) Using a One-Step Co-Precipitation Method Magnesium nitrate 257 g and aluminium nitrate 189 g were stirred in 1000 ml deionised water in a round bottomed flask, under $N_2$ until they had dissolved. In a separate container, the active anionic compound Ibuprofen 258 g was dissolved with stirring in 1500 ml of deionised water under $N_2$, and the pH was adjusted to 10.0 using 2M sodium hydroxide solution. The Ibuprofen solution was then heated to 80° C. and once up to temperature, the aqueous metal nitrate solution was added drop-wise using an addition funnel and the mixture was stirred vigorously. The pH was maintained at between 9.5 and 13 throughout the period of addition, using 2M sodium hydroxide solution via a second addition funnel. Addition of the Ibuprofen solution was complete within 30 minutes to 2 hours. Following complete addition, the reaction mixture was stirred for a further 10 minutes under $N_2$ and then allowed to cool to room temperature. The resultant LDH-Ibuprofen compound was isolated from the reaction mixture using vacuum filtration, ensuring that the recovered solid product was washed at least twice with 1000 ml of deionised water. Solid Ibuprofen Aluminium Magnesium Hydroxide (200 g) was obtained. FIG. 2 shows a typical XRP Diffractogram for this product material.

EXAMPLE 3

Attempt to Optimise the Robustness of the Structure of the Ibuprofen Aluminium Magnesium Hydroxide Material from Example 2 Using a Hydrothermal Treatment Step Method as Described in US2010/0233286 A1

Figure 3:
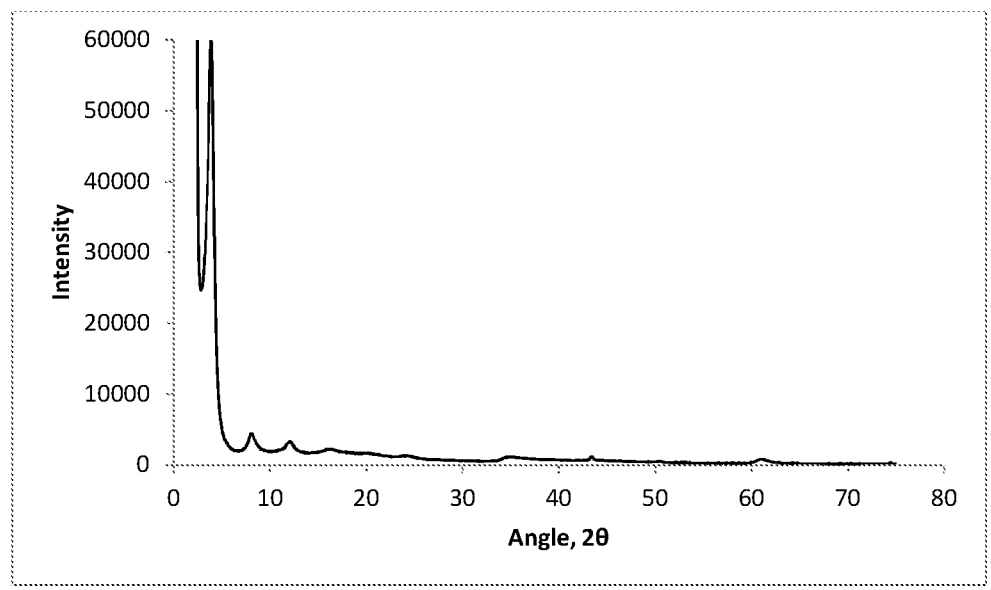
FIG. 3 shows a typical X-Ray Powder Diffractogram of LDH-Ibuprofen material produced by Co-precipitation method followed by a hydrothermal treatment as described in US2010/0233286 A1.

Starting Materials:
Ibuprofen aluminium magnesium hydroxide compound (200 g) obtained from the method of Example 2.
Method:
The solid product obtained from Example 2 was dispersed in 3750 ml deionised water as evenly as possible, and the dispersion was heated at 150° C. for 1-4 hours in an autoclave. The suspension was then cooled to room temperature, and the recovered solid product filtered, washed with 1000 ml deionised water and then air dried. A typical XRP Diffractogram for this product is shown in FIG. 3.

EXAMPLE 4

Figure 4:
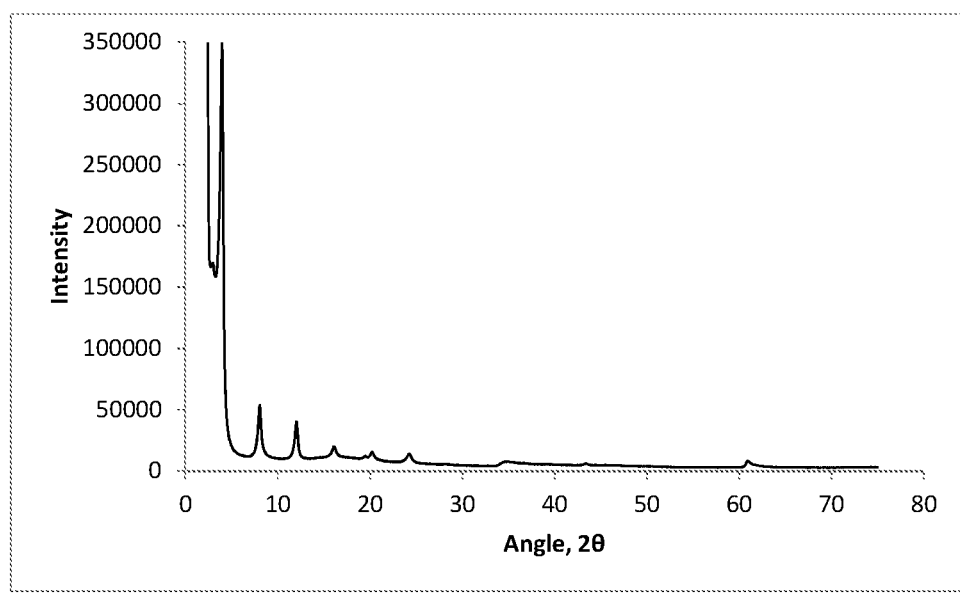
FIG. 4 shows a typical X-Ray Powder Diffractogram of LDH-Ibuprofen material produced by a Co-precipitation method followed by the process according to the present invention for preparing an improved LDH-Ibuprofen material.

Optimising the Robustness of the Structure of the Ibuprofen Aluminium Magnesium Hydroxide Material from Example 2 Using the Method of the Present Invention to Produce Improved LDH-Ibuprofen Material Starting Materials:
Ibuprofen Aluminium Magnesium Hydroxide compound (200 g) obtained from the method of Example 2.
Method:
The solid product obtained in Example 2 was dispersed as evenly as possible in 3750 ml of deionised water in an autoclave and heated to 150° C. for 2 hours under $N_2$ with stirring. The reaction mixture was then cooled to room temperature, and the solid removed by vacuum filtration. The solid was then washed with 1000 ml deionised water and 1000 ml methanol. The lumps were broken up and the solid was dried with stirring under vacuum at 60° C., until a constant weight was achieved. A typical XRP Diffractogram for this material is shown in FIG. 4.

Results: Determination of the Particle Robustness Factor for the Ibuprofen Aluminium Magnesium Hydroxide Compound Produced in Examples 1, 2, 3 and 4.

Samples of Ibuprofen Aluminium Magnesium Hydroxide compound were prepared using one of the four methods described in Examples 1, 2, 3 and 4 above, and each was analysed using X-ray diffraction techniques. The XRP Diffractograms for these materials are given in FIGS. 1, 2, 3, and 4 respectively. The Scherrer equation was then used to determine the value of tau for each of the four most dominant peaks in the X-ray diffraction pattern, and from this an average value of tau (the Particle Robustness Factor, PRF) across these four most dominant peaks was calculated for each sample of LDH-Ibuprofen compound. All tau values were normalised using a zero background intensity silicon wafer standard. The Results are presented below in Tables 1, 2, 3 and 4.

Typical operating conditions used to obtain the X-ray diffraction patterns are as follows:
Slit sizes: Divergence slit fixed: 2, Receiving slit: 1.52
Range: 2-75° 2θ
x-ray wavelength=K-Alpha1 wavelength: 1.540598, K-Alpha2 wavelength: 1.544426
Scan type: Continuous
Scan step size (°2θ):0.0334225 Time per step (secs): 280.035.

TABLE 1

Ion-Exchange (EXAMPLE 1)

| | θ, degrees | θ, radians | β, radians | T, Tau |
|---|---|---|---|---|
| Peak 1 (003) | 2.0409 | 0.035620425 | 0.184 | 5.438232 |
| Peak 2 (006) | 4.0679 | 0.070998249 | 0.4015 | 2.496951 |
| Peak 3 (009) | 6.00755 | 0.104851527 | 0.4015 | 2.504414 |
| Peak 4 (0012) | 8.0593 | 0.14066132 | 0.5353 | 1.886746 |
| | | | | Average (PRF) 3.081586 |

TABLE 2

One-Step Co-precipitation (EXAMPLE 2)

| | θ, degrees | θ, radians | β, radians | T, Tau |
|---|---|---|---|---|
| Peak 1 (003) | 1.9963 | 0.034842008 | 0.1338 | 7.47838 |
| Peak 2 (006) | 4.03385 | 0.070403964 | 0.4723 | 2.122557 |
| Peak 3 (009) | 5.9926 | 0.104590601 | 0.5038 | 1.995821 |
| Peak 4 (0012) | 7.98685 | 0.139396829 | 0.3779 | 2.672122 |
| | | | | Average (PRF) 3.56722 |

TABLE 3

One-Step Co-precipitation Followed by Hydrothermal Treatment (EXAMPLE 3)

| | θ, degrees | θ, radians | β, radians | T, Tau |
|---|---|---|---|---|
| Peak 1 (003) | 2.0089 | 0.035061919 | 0.2249 | 4.449155 |
| Peak 2 (006) | 4.0565 | 0.070799281 | 0.1875 | 5.346728 |
| Peak 3 (009) | 6.07215 | 0.10597901 | 0.3374 | 2.980564 |
| Peak 4 (0012) | 8.1694 | 0.142582928 | 0.5248 | 1.925022 |
| | | | | Average (PRF) 3.675367 |

TABLE 4

One-step co-precipitation followed by the Optimisation Method of the Present Invention (EXAMPLE 4)

| | θ, degrees | θ, radians | β, radians | T, Tau |
|---|---|---|---|---|
| Peak 1 (003) | 2.0014 | 0.03493102 | 0.1288 | 7.768714 |
| Peak 2 (006) | 4.0332 | 0.070392619 | 0.1473 | 6.805721 |

TABLE 4-continued

One-step co-precipitation followed by the Optimisation
Method of the Present Invention (EXAMPLE 4)

| | θ, degrees | θ, radians | β, radians | T, Tau |
|---|---|---|---|---|
| Peak 3 (009) | 6.0405 | 0.105426613 | 0.1473 | 6.82677 |
| Peak 4 (0012) | 8.0891 | 0.141181428 | 0.1288 | 7.842 |
| | | | | Average (PRF) 7.310801 |

As is clearly observed from a comparison of the average tau values presented in the Tables 1 to 4 above, the particle optimisation method of the present invention (Example 4) is extremely surprisingly significantly more efficient at producing highly robust LDH-Ibuprofen compounds than either the hydrothermal process employed in Example 3 (taken from the method described in US 2010/0233286) or the ion-exchange process used in Example 1 (as described in EP1 341 556). Therefore these results demonstrate that the optimisation process of the present invention is highly effective at producing remarkably robust particles.

Also as discussed above, the Applicant has found that such materials are particularly useful at reducing and or eliminating leaching of the intercalated anionic material from the LDH-Ibuprofen compound. The % w/w amount of active anionic compound that leaches from the LDH-active anion material may be determined using any convenient leaching method known in the art, for example as described in EP1341556B1.

Results:

The % w/w amount of Ibuprofen which leaches from samples of LDH-Ibuprofen materials prepared in Examples 1-4 was determined using standard analytical tools and presented in Table 5 below, together with taste data to show how effective each sample is at providing a formulation with low or no taste.

TABLE 5

| METHOD USED TO PREPARE IBUPROFEN ALUMINIUM MAGNESIUM HYDROXIDE (LDH-ACTIVE ANION COMPOUND) | LEACHATE, % w/w | BURN, IRRITATION OR POOR TASTE PRESENT? |
|---|---|---|
| Ion Exchange (Example 1) | Not tested | YES |
| One-step Co-precipitation (Example 2) | 6.2 | YES |
| One-step Co-precipitation followed by hydrothermal treatment from US2010/0233286 (Example 3) | 10.7 | YES |
| One-step Co-precipitation followed by the optimisation method of the present invention (Example 4) | 0.7 | NO |

The above results show that particle optimisation process of the present invention (Example 4) produces improved LDH-Ibuprofen materials which are capable of retaining almost 100% of the intercalated active anionic compound with only 0.7% w/w of ibuprofen leaching out.

This result compares extremely favourably against the 10.7% w/w ibuprofen which was observed to leach from materials treated with the hydrothermal process of Example 3. Indeed the above results indicate that the hydrothermal treatment method described in US2010/0233286 actually increases the amount of ibuprofen that leaches from the material made in Example 2.

In addition to this, the above leaching tests were conducted on samples where the deionised water had been in contact with the LDH-ibuprofen for 5 minutes. A parallel experiment in which the deionised water was in contact for 30 minutes produced identical low leaching level results (0.7% w/w) for the improved LDH-active anion material of the present invention. This is a clear demonstration that the ibuprofen is not continuously released from the improved LDH-active anion materials of the present invention and that the 0.7% w/w recorded is the total amount of material leached in the absence of ion exchange conditions and at a pH>4.

As the results in Table 5 also demonstrate, the burn/poor taste associated with ibuprofen is detectable in the mouth when the leaching level is 6.2% w/w, but not detected when the ibuprofen leaching level is 0.7% w/w. Thus 0.7% w/w ibuprofen as determined by the above leaching test is advantageously below the threshold for bitter taste/irritation detection by humans, and consequently the improved LDH-active anion materials of the present invention are highly suitable for use in the preparation of taste, burn and/or irritation masked formulations.

The invention claimed is:

1. A treatment process for preparing a treated layered double hydroxide-active anion material comprising a layered double hydroxide material intercalated with one or more active anions, comprising the steps:
   a) dispersing a layered double hydroxide-active anion starting material in a liquid dispersant, then heating and agitating the resulting suspension for a period of between 2 to 72 hours, at a specific temperature or over a range of temperatures, above 80° C. to 200° C.;
   b) cooling the heated suspension and separating the heat treated layered double hydroxide-active anion material from the suspension;
   c) washing the heat treated layered double hydroxide-active anion material one or more times with water and then a further washing liquid, and then drying the washed heat treated layered double hydroxide-active anion material at an elevated temperature of at least 50° C., and optionally under vacuum, to thereby yield the treated layered double hydroxide-active anion material;
   wherein the treated layered double hydroxide-active anion material consists of mixed hydroxides of one or more trivalent metal cations and one or more divalent metal cations, having an excess positive charge that is balanced by one or more intercalated active anions, and wherein the one or more divalent metal cations are selected from the group consisting of $Co^{2+}$, $Ni^{2+}$, $Cu^{2+}$, $Zn^{2+}$, $Mn^{2+}$, $Pd^{2+}$, $Ti^{2+}$, $Ca^{2+}$, $Cd^{2+}$, and $Mg^{2+}$.

2. A process according to claim 1, wherein drying in step c) comprises drying with agitation.

3. A treated layered double hydroxide-active anion material made by the treatment process of claim 1.

4. A treated layered double hydroxide-active anion material according to claim 3 combined with one or more pharmaceutically acceptable excipients.

5. A treated layered double hydroxide-active anion material according to claim 3, wherein the one or more intercalated active anions are derived from compounds selected from the group consisting of NSAIDS, gaba-analogues, antibiotics, statins, angiotensin-converting enzyme (ACE) inhibitors, antihistamines and dopamine precursors, anti-microbials, psychostimulants, prostaglandins, anti-depressants, anti-convulsants, coagulants, anti-cancer agents, immuno-suppressants, laxatives, dye compounds, agrochemicals, medicaments and food supplements and molecules or compounds used in food, beverages and pharmaceuticals.

6. A treated layered double hydroxide-active anion material according to claim 3, comprising one or more intercalated active anions derived from compounds selected from Ibuprofen, Naproxen and Diclofenac.

7. A treated layered double hydroxide-active anion material according to claim 3, comprising one or more intercalated active anions which are derived from poor tasting or irritating substances.

8. A formulation comprising a treated layered double hydroxide-active anion material made according to the process of claim 1 selected from the group consisting of dry granules, tablets, caplets, aqueous or non-aqueous liquids or suspensions, orally disintegrating tablets, orally disintegrating granules, lozenges, films, capsules, powders, effervescent formulations, buccal and sub-lingual formats, gels, syrups and gums.

9. A method of producing a formulation comprising formulating one or more treated layered double hydroxide-active anion materials made according to the process of claim 1, in a form selected from the group consisting of dry granules, tablets, caplets, aqueous or non-aqueous liquids or suspensions, orally disintegrating tablets, orally disintegrating granules, lozenges, films, capsules, powders, effervescent formulations, buccal and sub-lingual formats, gels, syrups and gums.

10. A method of producing a formulation according to claim 9, which exhibits a substantially zero taste sensation, burn or irritation, within the mouth, buccal cavity, larynx or gastrointestinal tract of the consumer or patient, comprising formulating one or more treated layered double hydroxide-active anion materials made according to the process of claim 1 in a form selected from the group consisting of dry granules, tablets, caplets, aqueous or non-aqueous liquids or suspensions, orally disintegrating tablets, orally disintegrating granules, lozenges, films, capsules, powders, effervescent formulations, buccal and sub-lingual formats, gels, syrups and gums.

11. The treated layered double hydroxide-active anion material according to claim 3, wherein one or more intercalated active anions are configured to leach a total of less than 5% by weight into a solvent suitable for dissolving the one or more active anions, in the absence of ion exchange conditions and/or at a pH>4.

* * * * *